United States Patent [19]

Koyama et al.

[11] 4,249,540
[45] Feb. 10, 1981

[54] OPTICAL SOMATO-MEASURING APPARATUS

[75] Inventors: Tomiyasu Koyama; Masashi Horimoto; Midori Horimoto, all of Sapporo, Japan

[73] Assignee: President of Hokkaido University, Hokkaido, Japan

[21] Appl. No.: 30,887

[22] Filed: Apr. 17, 1979

[30] Foreign Application Priority Data

Apr. 24, 1978 [JP] Japan ................................ 53/48490

[51] Int. Cl.³ ............................................. A61B 5/02
[52] U.S. Cl. .................................. 128/666; 128/633; 128/691; 356/27
[58] Field of Search ........................... 128/665–667, 128/691, 633; 356/381, 382, 27

[56] References Cited

U.S. PATENT DOCUMENTS

| 3,313,290 | 4/1967 | Chance et al. | 128/633 |
| 3,511,227 | 5/1970 | Johnson | 128/666 |
| 3,693,025 | 9/1972 | Brunton | 356/382 |
| 4,109,647 | 8/1978 | Stern et al. | 128/666 |

OTHER PUBLICATIONS

Journ. of Clinical Science, vol. 13, No. 9, (1977), pp. 1197–1202.

Primary Examiner—Kyle L. Howell
Attorney, Agent, or Firm—Robert E. Burns; Emmanuel J. Lobato; Bruce L. Adams

[57] ABSTRACT

An optical apparatus for somato-measuring such as measuring of fluid velocity in a minute blood vessel by a laser Doppler microscope, comprises a laser supplying at least two laser beams through a transparent sheet provided on the surface of a living object to be measured, the transparent sheet having a refractive index approximated to that of the object in order to avoid reflected lights from the surface of the object and to measure necessary lights scattered by the internal part of the object.

3 Claims, 6 Drawing Figures

OPTICAL SOMATO-MEASURING APPARATUS

BACKGROUND OF THE INVENTION

This invention relates to optical somato-measuring apparatus that draws information about the internal tissues of a living body, such as the intravascular bloodstream velocity, using laser beams.

Various apparatus obtain information about the internal tissues of an object by throwing a beam of light on the object and measuring the light scattered by the internal tissue. These apparatus require a light source that supplies a beam of light to the object and a photometer to measure the light scattered therefrom. Ordinarily, the light source and photometer are disposed on the same side. This arrangement is known as the reflection type. In the reflection type apparatus, however, the photometer receives a strong light reflected from the surface of the object, along with the scattered light from the internal tissue thereof that is to be measured. Accordingly, it becomes very difficult to make accurate measurement of the scattered light from the internal tissue.

Laser microscopes and other similar modern optical apparatus are in practical use. As this type of optical measurements are increasing, such apparatus will find increasingly wide application. But they also encounter the aforesaid problem of reflection from the object surface. That is, the measuring device cannot accurately measure the scattered light, receiving the surface-reflected light that has nothing to do with the minute tissues inside the object.

Now an application to the laser Doppler microscope will be described. First, a beam of light, 10 to 40 μm, emitted from a laser is divided into two light-beams, using a prism etc. The two light-beams are intersectingly thrown on, for example, a minute blood vessel in a living tissue through an optical system comprising a set of microscope lenses. Blood cells in the blood vessel scatter the thrown light-beams. Consequently, the two incident lights cause Doppler deviations according to their respective incident angles and the flow rate of the blood cells, whereby the frequency of the lights is slightly changed. By measuring the lights scattered by the blood cells with a photomultiplier incorporated in the microscope, information corresponding to the bloodstream velocity is obtained. If the microscope is focused on a point where the two laser beams intersect, the beat frequency of the two Doppler-deviated lights is taken out in the form of an electric signal. This frequency theoretically is proportional to the bloodstream velocity in the minute blood vessel.

DESCRIPTION OF THE PREFERRED EMBODIMENTS

Figure 1:
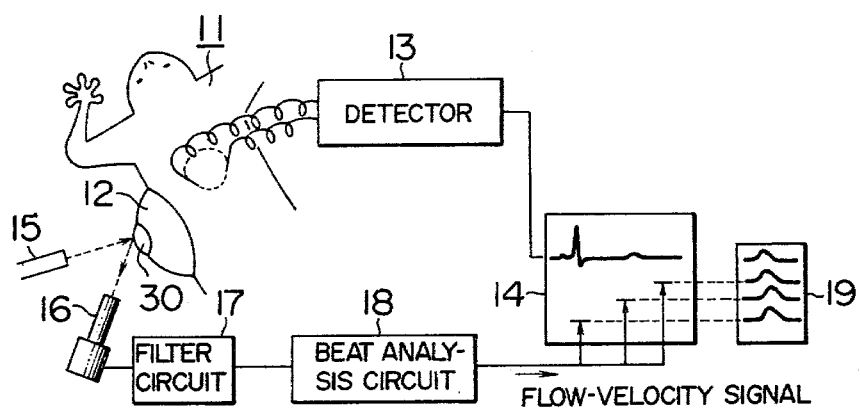
FIG. 1 illustrates optical somato-measuring apparatus.

FIG. 1 shows the measuring of the bloodstream velocity in the minute blood vessel in a lung 12 of a frog 11. A chest wall of the frog 11 is cut open to expose the lung 12. At the same time, an electrocardiogram of the frog 11 is obtained by a detector 13 to determine the R wave corresponding to the heartbeat. Then, a standard R-wave occurrence timing signal is supplied to a time-sharing control circuit 14.

According to the conventional methods, a laser 15 throws laser beams direct on the lung 12, without interposing a transparent sheet 30 therebetween. As mentioned before, two laser beams are intersectingly thrown on an object minute blood vessel in the lung 12. A microscope is focused on a point where the two light-beams on the minute blood vessel intersect, so that the microscope detects the light scattered by blood cells in the minute blood vessel. Receiving this scattered light, a photomultiplier 16 takes out the beat frequency Doppler-deviated according to the bloodstream velocity in the form of an electric signal. A filter circuit 17 removes unnecessary noise signals etc. contained in the electric signal. A beat analysis circuit 18 converts the signal drawn from the filter circuit 17 into a beat frequency signal, which is supplied to the time-sharing control circuit 14 as a flow-velocity signal.

This time-sharing control circuit 14 divides the input flow-velocity signal by, for example, 60-millisecond increments, starting when the detector 13 detects the occurrence of the R wave. The circuit 14 collects data represented by the flow-velocity signal in the first half of each increment, outputs the wave-crest interval of the measured flow-velocity signal wave as a time signal, and gives an integrated recording for each increment on a histogram recorder 19.

The blood cells in the minute blood vessel do not flow at a constant velocity even at the same time point of the heartbeat cycle where the R wave occurs. Therefore, the flow-velocity versus occurrence-frequency histograms on the recorder 19 becomes as shown in FIG. 2.

Figure 2:
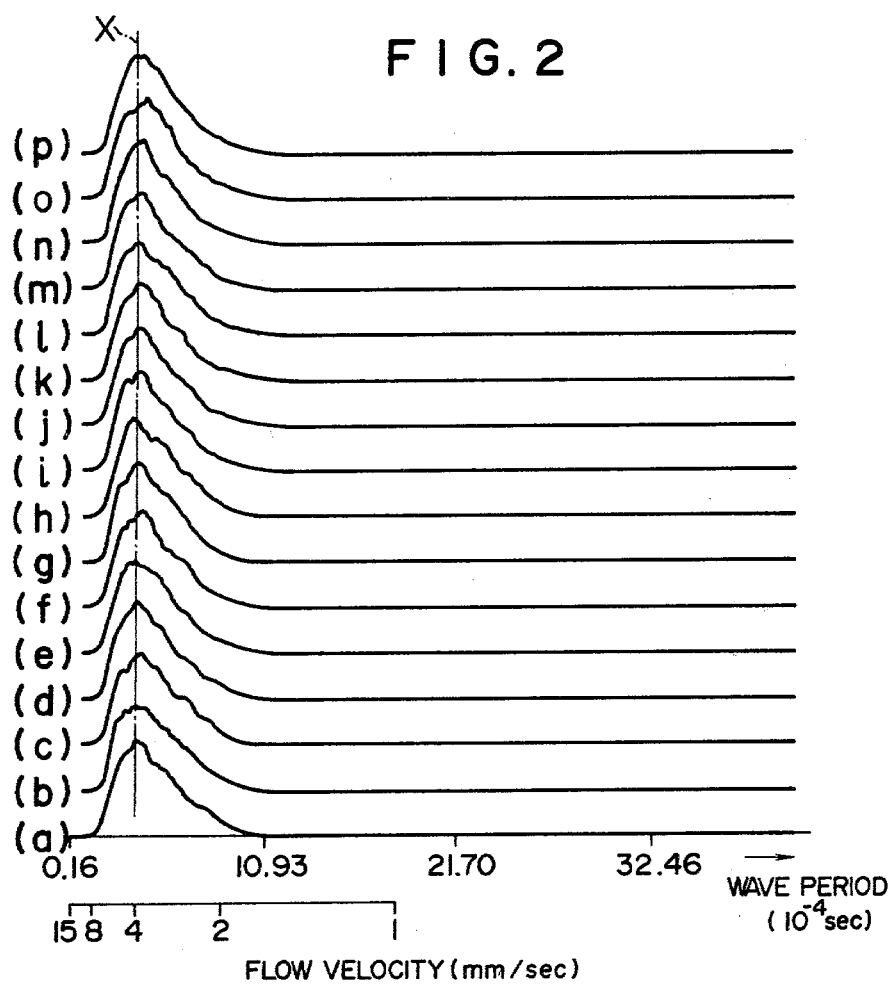
FIG. 2 is a flow-velocity versus occurrence-frequency histogram showing an example of conventional measurement results.

FIG. 2 shows 16 histograms, (a) through (p). The lowest histogram (a) represents a bloodstream velocity and its occurrence frequency derived from the bloodstream velocities measured during the 0-to-30millisecond period immediately after the occurrence of the R wave for tense of heartbeats. Likewise, the histograms (b) and (c) represent the bloodstream velocities and their occurrence frequencies for the 60-to-90-millisecond and 120-to-150-millisecond periods, respectively. The 16 histograms are seperated by 60-millisecond increments following the occurrence of the R wave or the start of heart-contraction (data collection is done in the 30-millisecond period corresponding to the first half of each increment). The highest histogram (p) is for the 900-to-930-millisecond period after the occurrence of the R wave.

In FIG. 2, the horizontal axis represents a wave period or a wave-crest interval of a beat frequency signal given by $10^{-4}$-second increments. It shows flow velocity versus wave period. If wave period is T, its relationship with flow velocity is expressed as $$\text{Flow velocity} = a(1/T)$$

where a=a function of an angle at which the two laser beams intersect, which is a constant depending on the beam throwing condition.

In FIG. 2, a line X, connecting the peaks of the top and bottom histograms (p) and (a), is given to permit comparing all histograms. The histograms in FIG. 2 shows little change with the heartbeat cycle. In measuring, the two laser beams are intersected on the minute artery of the lung 12. The microscope to gather the light scattered by the blood cells in the artery to the photomultiplier 16 is focused on the minute artery. In spite of that, no signal indicating the bloodstream velocity is measured. That is, the light reflected from the surface of the object is preventing the measurement of the light scattered by the minute artery.

In view of the above-described difficulty, this invention provides optical somato-measuring apparatus that permits accurate and sure detection of information. The object of this invention is achieved by providing a transparent sheet on the surface of the object. By this means, a photomultiplier etc. can detect the scattered light that is clearly separated from the surface-reflected light.

Now an embodiment of this invention will be described by reference to the accompanying drawings. As shown in FIG. 1, a transparent sheet 30 of hydrated plastic is placed on the surface of the lung 12 to be measured. It is through this transparent sheet 30 that the laser beams are thrown and the photomultiplier 16 detects the scattered light.

Figure 3:
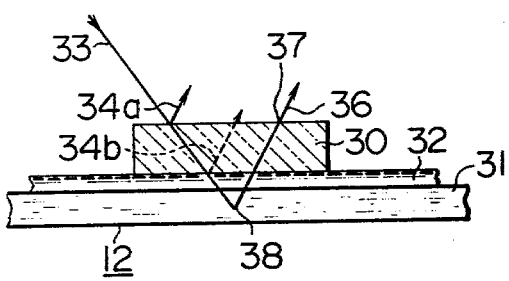
FIG. 3 is a partly cross-sectional view showing details of an embodiment of this invention.

FIG. 3 is an enlarged view showing the part being measured. Reference numeral 31 designates a blood vessel being measured. The transparent sheet 30 is placed on the external surface of the blood vessel 31 or, more concretely, on the exposed surface of the lung 12, with a film 32 of a physiological solution of salt or sodium chloride therebetween. Laser beams 33 are thrown aslant onto the transparent sheet 30. Although FIG. 3 shows only one beam, two laser beams 33 are thrown actually, from two directions and at, for example, the same incident angle, so as to intersect in the blood vessel 31.

When the laser beams 33 are thus thrown, the surfaces of the transparent sheet 30 and the object being measured emit reflected lights as indicated by reference characters 34a and 34b in FIG. 3. Having nothing to do with the bloodstream velocity in the blood vessel 31, these reflected lights are unnecessary signals.

The scattered light 36 from the blood vessel 31 appears on the transparent sheet 30, but in a position 37 away from the unnecessary reflected lights. With its field of vision set on this position 37, the microscope is focused on a position 38 where the two laser beams intersect, and the photomultiplier 16 is set to observe the scattered light 36. Then the photomultiplier 16 can measure the necessary scattered light 36 only. The unnecessary reflected lights 34a and 34b are perfectly removed.

Figure 4:
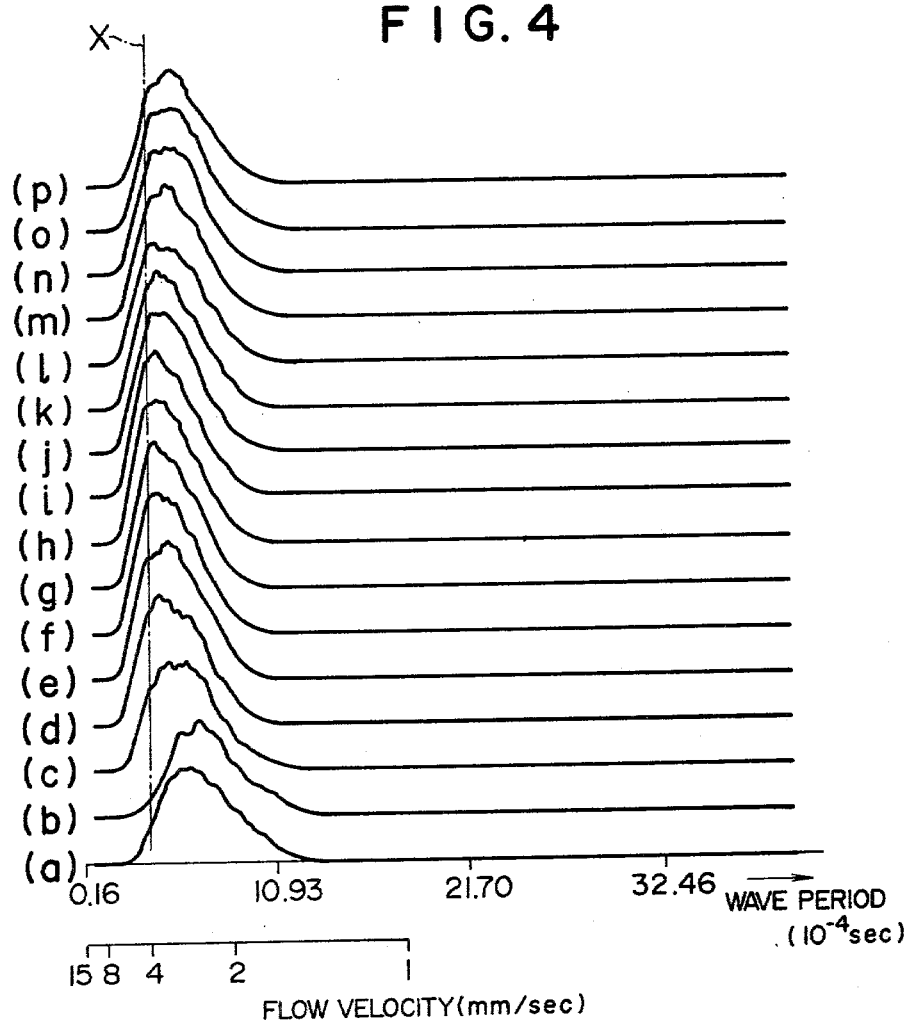
FIG. 4 is a flow-velocity versus occurrence-frequency histogram according to this invention.

FIG. 4 shows histograms similar to FIG. 2 but measured by the above-described apparatus of this invention. Looking up along a line X, a definite difference between FIG. 4 and FIG. 2 can be found. Obviously, the histograms begin to move to the high-velocity side at (c) or 120 milliseconds after the occurrence of the R wave, indicate the highest value at (h) or after 420 milliseconds, and then gradually return to the low-velocity side.

Figure 5:
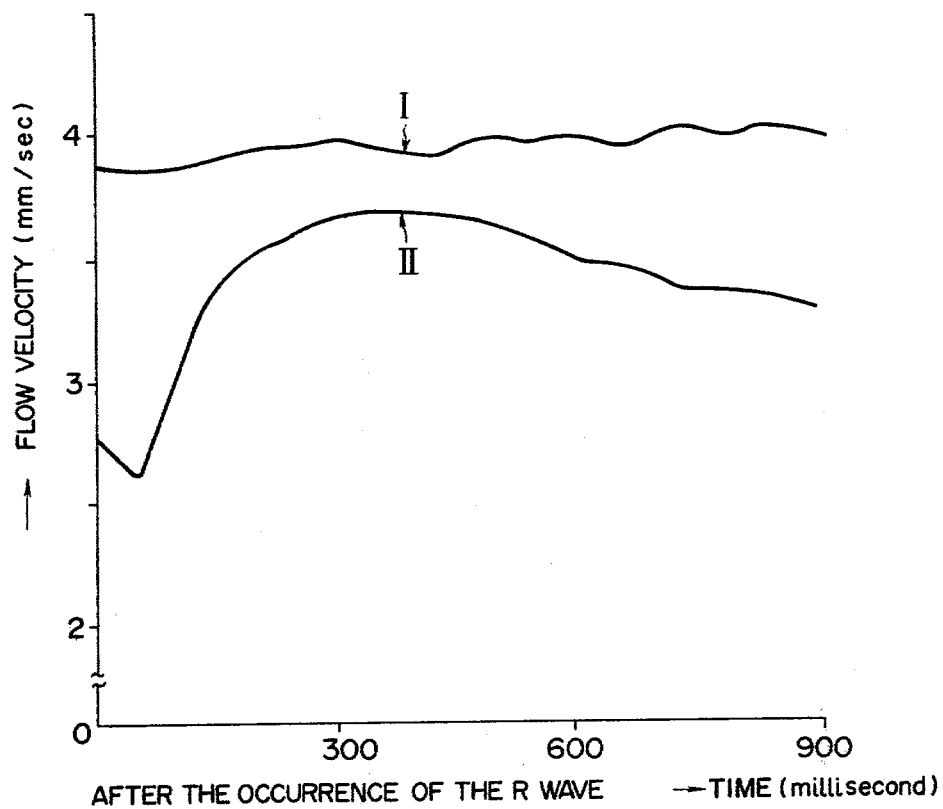
FIG. 5 compares a conventional measurement and one according to this invention, using curves showing the relationship between elapsed time and mean flow velocity.

Curves (I) and (II) in FIG. 5 compare the conventional measurement in FIG. 2 and the one according to this invention in FIG. 4, by means of the relationship between the time elapsed after the occurrence of the R wave and the mean flow velocity determined from the histograms (a) through (p). The curve (II) obtained according to the present invention evidently shows the pulsation of the bloodstream in the minute blood vessel or artery 31 being measured.

Figure 6:
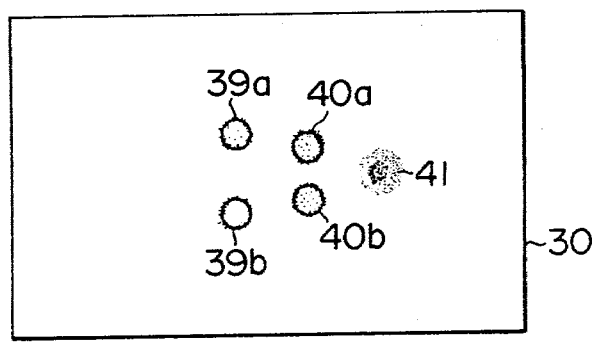
FIG. 6 shows a measuring plane according to this invention.

FIG. 6 shows the optical effect of the above-described measuring apparatus. The part irradiated with the laser beams is viewed from the photomultiplier. Light spots 39a and 39b, on the left, are total reflections made by the two laser beams from the light source on their incidence plane at the surface of the transparent sheet 30 of hydrated plastic placed on the surface of the object being measured. Light spots 40a and 40b, in the middle, are reflections made at the interface between the back side of the transparent sheet 30 and the physiological solution of salt that is interposed between the back side and the lung tissue. The light spots 40a and 40b are sufficiently darker, and located closer to each other, than the light spots 39a and 39b. On the right is a bright spot 41 that is formed by the two light beams focused into one point on the artery and scattered under the influence of Doppler deviation. Here, the tissue of the lung is hardly visible, because the area illuminated by the laser beams is very limited.

By placing this bright spot 41 at the center of the microscope view field, only the desired scattered light enters the photomultiplier, which permits accurate measurement and output of flow-velocity signals.

If the transparent sheet 30 were absent, the reflections at the four light spots 39a, 39b, 40a and 40b would agree with the bright spot 41 formed by the scattered light, whereupon the reflected light, which is much stronger than the scattered light, would enter the photomultiplier. Consequently, detection of the Doppler-deviated frequency, therefore the desired optical measurement, would become impossible.

This elimination of the unnecessary reflection surface from the scattered light measuring plane is applicable to various optical measurements. For example, it can be used for the measurement of image forming performance if a suitable coating material is selected to prevent the refraction of light.

As evident from the above, this invention permits easy and effective optical measurement of living bodies. Especially it assures the measurement of only the scattered light at the desired point, eliminating the unnecessary reflected light from the incoming light beam.

We claim:

1. Optical somato-measuring apparatus comprising, means for providing a transparent sheet positionable on the surface of a living object to be diagnosed, the transparent sheet having a refractive index approximating that of the object to be diagnosed, means for supplying through the transparent sheet at least two laser beams intersecting at a measuring point within the living object being diagnosed, and means for observing the scattered light from a diagnostic point appearing at a point on the transparent sheet that is different from the points of incidence of the laser beams.

2. Optical somato-measuring apparatus according to claim 1, wherein the transparent sheet comprises a sheet of hydrated plastic.

3. Optical somato-measuring apparatus according to claim 1, wherein the transparent sheet is placed on the surface of the living object with a film of a physiological solution of salts interposed thereunder.

* * * * *